United States Patent [19]

Almgren et al.

[11] Patent Number: 5,034,411

[45] Date of Patent: Jul. 23, 1991

[54] NOVEL 4-CYANOPHENYL DERIVATIVES WITH ACTION AGAINST CARDIAC ARRHYTHMIC

[75] Inventors: Olle K. S. Almgren, Göteborg; Göran B. D. Duker, V. Frölunda; Gert C. Strandlund, Mölndal, all of Sweden

[73] Assignee: Aktiebolaget Hassle, Sweden

[21] Appl. No.: 289,630

[22] Filed: Dec. 22, 1988

[30] Foreign Application Priority Data

Dec. 23, 1987 [SE] Sweden .................. 8705150

[51] Int. Cl.$^5$ .................. A61K 31/275; C07C 255/50
[52] U.S. Cl. .................. 514/522; 514/524; 558/413; 558/415; 558/422
[58] Field of Search .................. 558/413, 422, 415; 514/523, 522, 524

[56] References Cited

U.S. PATENT DOCUMENTS 4,544,654 10/1985 Davey et al. .................. 514/212 X

FOREIGN PATENT DOCUMENTS

| 0017893 | 10/1980 | European Pat. Off. . |
| 0195396 | 9/1986 | European Pat. Off. . |
| 0206747 | 12/1986 | European Pat. Off. . |
| 0245997 | 11/1987 | European Pat. Off. . |
| 1593771 | 4/1967 | Fed. Rep. of Germany . |
| 2503222 | 7/1976 | Fed. Rep. of Germany . |
| 2280376 | 2/1976 | France . |
| 404793 | 10/1978 | Sweden . |
| 421123 | 11/1981 | Sweden . |
| 570368 | 10/1975 | Switzerland . |
| 952547 | 3/1964 | United Kingdom . |
| 1433920 | 4/1976 | United Kingdom . |
| 1457876 | 12/1976 | United Kingdom . |

OTHER PUBLICATIONS

Morrison et al., "Organic Chemistry", (1959), p. 553, Allyn and Bacon, Inc., Boston.
Williams, "Classification of Anti-Arrythmic Drugs"; pp. 449–472.
Foye, "Principles of Medicinal Chemistry", 2nd ed., (1981), Lea & Febiger, Philadelphia, pp. 384–385.
Weng et al., "Antiarrhythmic Drugs: Electrophysiological Basis of Their Clinical Usage", pp. 106–112 (1986).

Primary Examiner—Joseph Paul Brust

[57] ABSTRACT

This application relates to novel 4 cyanophenyl derivatives which are useful for the treatment of cardiac arrhythmia and pharmaceutical compositions containing these compounds as the active ingredients.

8 Claims, No Drawings

NOVEL 4-CYANOPHENYL DERIVATIVES WITH ACTION AGAINST CARDIAC ARRHYTHMIC

DESCRIPTION

1. Field of the Invention

The present invention relates to novel, pharmacologically active compounds and to processes for their preparation. The invention also relates to pharmaceutical compositions containing the compounds and to methods of their pharmacological use.

The object of the invention is to provide substances useful in the treatment, acute as well as long term, of cardiac arrhythmias of diverse etiology.

2. Background Art

GB 1 433 920 discloses compounds of the formula

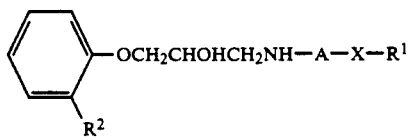

wherein $R^1$ for instance stands for an alkyl or cycloalkyl radical or an aryl radical, $R^2$ for instance stands for halogen, CN or $NO_2$ radical, A stands for an alkylene radical of from 2 to 6 carbon atoms and X stands for —S—, —SO— or —$SO_2$— radical.

These compounds are said to possess β-adrenergic blocking acitivty.

GB 1 457 876 discloses among others the compounds

and

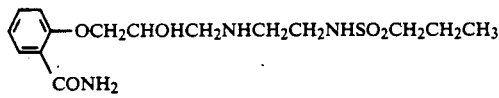

These compounds are said to possess β-adrenergic blocking activity.

DISCLOSURE OF THE INVENTION

The present invention concerns new compounds useful for treatment, acute as well as long term, of cardiac arrhythmics of diverse etiology.

An object is to provide antiarrhythmics which have less prominent side effects than existing antiarrhythmic drugs. The compounds should for instance be free of negative inotropic effect and the compounds may even be positively inotropic. The compounds should further separate the antiarrhythmic effect from central nervous and gastrointestinal effects.

The compounds of the invention are characterized by the general formula

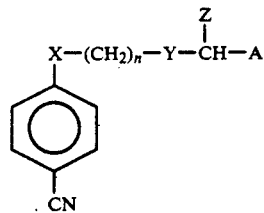

and when appropriate in the form of a racemic mixture or in the form of a stereoisomeric component and the pharmaceutically acceptable salts thereof, in which formula X is O, $CH_2$, CHOH, CO, CONH, NH, S, SO or $SO_2$, n is an integer 0, 1 or 2

Y is $(CH_2)_m$, CHOH, $CHOCH_3$, CHNHR or CHF m is an integer 0 or 1 and

R is hydrogen, methyl or ethyl,

Z is hydrogen or a saturated or unsaturated, straight or branched alkyl group containing 1-3 carbon atoms, A is a group

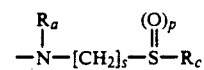

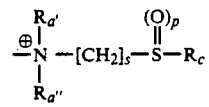

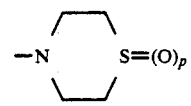

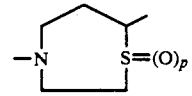

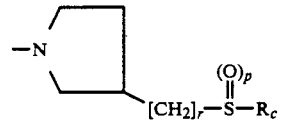

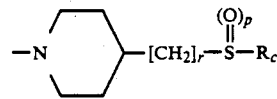

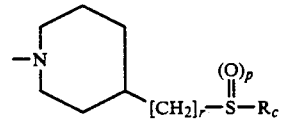

wherein $R_a$ is a straight or branched hydroxyalkyl or a straight or branched alkyl group containing 1-5 carbon atoms and optionally substituted by one or more fluoro atoms, $R_c$ is a saturated or unsaturated, straight or branched alkyl group containing 1-4 carbon atoms and optionally substituted by one or more fluoro atoms, a cycloalkyl or an alkylcycloalkyl group, containing 3-5 ring carbon atoms, an unsubstituted phenyl group or a phenyl group substituted by one or more substituents selected from the group consisting of fluoro, hydroxy, methoxy, ethoxy, CN, CONH$_2$, NHSO$_2$CH$_3$ R$_a$' is the same as R$_a$ and independently of R$_a$"
R$_a$" is the same as R$_a$ and independently of R$_a$'
p is an integer 0, 1 or 2,
r is an integer 0, 1, 2 or 3,
s is an integer 2, 3, 4 or 5
with the proviso that when X is 0 and
A is a group

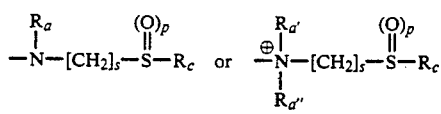

then R$_c$ is a cycloalkyl or an alkylcycloalkyl group, containing 3-5 ring carbon atoms, an unsubstituted phenyl group or a phenyl group substituted by one or more substituents selected from the group consisting of fluoro, hydroxy, methoxy, ethoxy, CN, CONH$_2$, NHSO$_2$CH$_3$.

Halogen atoms in formula I comprise fluorine, chlorine, bromine and iodine.

Alkyl groups in formula I which are straight and saturated are for instance methyl, ethyl, n-propyl, n-butyl.

Alkyl groups in formula I which are straight and unsaturated are for instance vinyl, allyl, propenyl, —C≡CH, —CH$_2$—C≡CH and —C≡CCH$_3$.

Alkyl groups in formula I which are branched and saturated are for instance i-propyl, s-butyl, i-butyl, t-butyl.

Alkyl groups in formula I which are branched and unsaturated are for instance

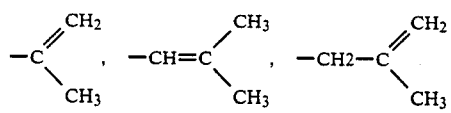

Alkyl groups in formula I which are substituted by fluorine are for instance 1-3 H changed for F in the definition for alkyl groups which are straight and saturated or branched and saturated, for instance CH$_2$CHFCH$_3$, CH$_2$CH$_2$CF$_3$, CH$_2$CF$_2$CH$_3$ etc.

Alkyl groups in formula I which are substituted by hydroxy are for instance CH$_2$—OH, CH$_2$—CH$_2$—OH,

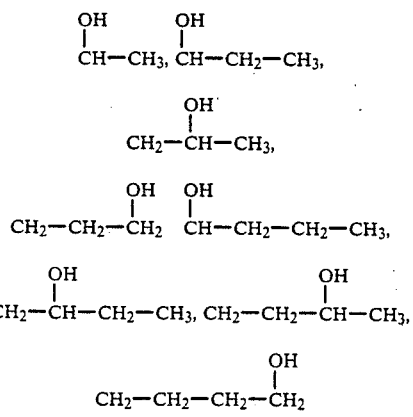

Cycloalkyl groups in formula I are for instance cyclopropyl, cyclobutyl, cyclopentyl.

Alkylcycloalkyl groups in formula I are for instance

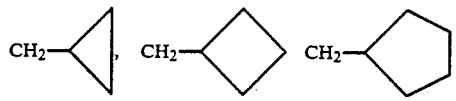

Substituted phenyl group in formula I would be substituted by one substituent in the ortho, meta or para position or by two substituents—the same or different—in the 2,3-position, 2,4-position, 2,5-position, 2,6-position, 3,4-position or 3,5-position, or by three substituents—the same or different—in the 2, 3, 4-position, 2, 3, 5-position, 2, 3, 6-position and 3,4,5-position.

Preferred groups of compounds of the invention are obtained when
X is O, CH$_2$, CHOH, CONH, NH
n is 0, 1
Y is CHOH, (CH2)m wherein m 0, 1
Z is hydrogen
A is a group

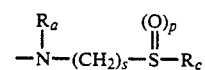

wherein R$_a$ is CH$_3$, C$_2$H$_5$, C$_3$H$_7$, CH$_2$CH$_2$OH, CH$_2$CHOHCH$_2$
s is 3, 4
p is 0, 1
R$_c$ is C$_2$H$_5$, C$_3$H$_7$, CH$_2$CHFCH$_3$, cyclopropylmethyl or an unsubstituted phenyl or a phenyl group substituted with OH, F, OCH$_3$, OC$_2$H$_5$ Particularly preferred groups of compounds of the invention are obtained when
X is 0
n is 1
Y is CHOH, (CH$_2$)$_m$ wherein m=1
Z is hydrogen
A is a group

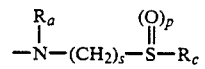

wherein R$_a$ is CH$_3$, C$_2$H$_5$, C$_3$H$_7$, CH$_2$CH$_2$OH
s is 3
p is 0, 1
R$_c$ is an unsubstituted phenyl group or a phenyl group substituted with OH, F, OCH$_3$, OC$_2$H$_5$ Other preferred groups of compounds of the invention are obtained when
X is CH$_2$
n is 0, 1
Y is CHOH, (CH$_2$)$_m$ where m=0, 1
Z is hydrogen
A is a group

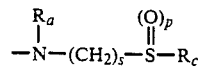

wherein R$_a$ is CH$_3$, C$_2$H$_5$, C$_3$H$_7$, CH$_2$CH$_2$OH, CH$_2$CHOHCH$_2$ s is 3
p is 0, 1
$R_c$ is $C_2H_5$, $C_3H_7$, $CH_2CHFCH_3$.

Quarternary nitrogen compound may be obtained from the compounds above by alkylation at the amino group.

Preferred compounds are
4-[3-[ethyl[3-(phenylthio) propyl]amino]-2-hydroxypropoxy]benzonitrile
4-[3-[ethyl[3-(phenylsufinyl) propyl]amino]-2-hydroxypropoxy]benzonitrile
4-[2-[ethyl[3-(propylthio)propyl]amino]-1-hydroxyethyl]-benzonitrile
4-[2-[ethyl[3-(propylsulfinyl)propyl]amino-]1-hydroxyethyl]benzonitrile
2-[[3-[[3-(4-cyanophenoxy)-2-hydroxypropyl]ethylamino]propyl]thio]benzamide
4-[3-[ethyl[3-[(4-hydroxyphenyl)thio]propyl]amino]-2-hydroxypropoxy]-benzonitrile
4-[2-hydroxy-3-(4-thiomorpholinyl)propoxy]benzonitrile
4-[2-hydroxy-3-(4-thiomorpholinyl)propoxy]-benzonitrile-S-oxide
4-[4-[(2-hydroxyethyl)[3-(propylthio)propyl]amino]-butyl]-benzonitrile
4-[4-[(2-hydroxyethyl)[3-(propylsulfinyl)propyl]amino]butyl]benzonitrile
4-[[3-[ethyl[3-(propylthio) propyl]amino]-2-hydroxypropyl]amino]-benzonitrile
4-[[3-[ethyl[3-(propylsulfinyl) propyl]amino]-2-hydroxypropyl]amino]-benzonitrile
4-cyano-N-[N'-isopropyl-N'-(3-propylthio)propyl]aminoethylbenzamide
4-[3-[ethyl[3-[(4-hydroxyphenyl)sulfinyl]propyl]amino]-2-hydroxypropoxy]-benzonitrile
4-[3-[ethyl[3-[(3-fluorophenyl)thio]propyl]amino]-2-hydroxypropoxy]-benzonitrile.

More preferred compounds are
4-[3-[ethyl[3-(phenylthio) propyl]amino]-2-hydroxypropoxy]benzonitrile
4-[3-[ethyl[3-(phenylsufinyl) propyl]amino]-2-hydroxypropoxy]-benzonitrile
4-[3-[ethyl[3-[(4-hydroxyphenyl)thio]propyl]amino]-2-hydroxypropoxy]-benzonitrile
4-[4-[(2-hydroxyethyl)[3-(propylthio)propyl]amino]-butyl]-benzonitrile
4-[4-[(2-hydroxyethyl)[3-(propylsulfinyl)propyl]amino]butyl]benzonitrile
4-[3-[ethyl[3-[(4-hydroxyphenyl)sulfinyl]propyl]amino]-2-hydroxypropoxy]-benzonitrile Particularly preferred compounds are
4-[4-[(2-hydroxyethyl)[3-(propylthio)propyl]amino]-butyl]-benzonitrile
4-[4-[(2-hydroxyethyl)[3-(propylsufinyl)propyl]amino]-butyl]benzonitrile.

In many instances the compounds of formula I occur in stereoisomeric forms, such forms being due to for instance optical isomerism, geometric isomerism and conformations of molecules.

The tertiary amines of the invention can be quarternarized with a lower alkyl group and the quarternary compounds have the same effect as the tertiary compounds.

The new compounds of this invention may be used therapeutically as a sterochemical mixture or in the stereochemical pure forms.

Pharmaceutical preparations

In clinical practice the compounds of the present invention will normally be administered orally, rectally or by injection in the form of pharmaceutical preparations comprising the active ingredient either as a free base or as a pharmaceutically acceptable non-toxic, acid addition salt, e.g. the hydrobromide, hydrochloride, phosphate, sulphate, sulphonate, sulphamate, citrate, lactate, maleate, tartrate, acetate and the like in association with a pharmaceutically acceptable carrier. Accordingly, terms relating to the novel compounds of this invention whether generically or specifically are intended to include both the free amine base and the acid addition salts of the free base, unless the context in which such terms are used, e.g. in the specific examples would be inconsistent with the broad concept.

The carrier may be a solid, semisolid or liquid diluent or capsule. These pharmaceutical preparations constitute a further aspect of this invention. Usually the active substance will constitute between 0.1 and 99% by weight of the preparation, more specifically between 0.5 and 20% by weight for preparations intended for injection and between 2 and 50% by weight for preparations suitable for oral administration.

To produce pharmaceutical preparations containing a compound of the invention in the form of dosage units for oral application, the selected compound may be mixed with a solid pulverulent carrier, e.g. lactose, saccharose, sorbitol, mannitol, starches such as potato starch, corn starch or amylopectin, cellulose derivatives, gelatine or other suitable tablet excipients, and a lubricant such as magnesium stearate, calcium stearate, sodium stearyl fumarate, polyethylene glycol waxes, and the like, and then compressed to form tablets. If coated tablets are required, the cores, prepared as described above, may be sugar coated or film coated by conventional film coating polymers.

Dyestuffs may be added to these coatings in order to readily distinguish between tablets containing different active substances or different amounts of the active compound.

For the preparation of soft gelatine capsules (pearl-shaped closed capsules) consisting of gelatine and for example, glycerol or similar closed capsules, the active substance may be admixed with a vegetable oil. Hard gelatine capsules may contain granulates of the active substance in combination with solid, pulverulent carrier such as lactose, saccharose, sorbitol, mannitol, starches (e.g. potato starch, corn starch or amylopectin), cellulose derivatives or gelatine or other suitable pharmaceutically acceptable constituents.

Dosage units for rectal application can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example solutions containing from about 0.2 to about 20% by weight of the active substance herein described, the balance being sugar alcohols and water optionally mixed with ethanol, glycerol, or propyleneglykol. Optionally such liquid preparations may contain colouring agents, flavouring agents, saccharine and, as a thickening agent, such as carboxymethylcellulose, hydroxypropylmethylcellulose or the like.

Solutions for parenteral applications by injection can be prepared in an aqueous solution of a water-soluble pharmaceutically acceptable salt of the active substance preferably in a concentration of from about 0.5 to about 10% by weight. These solutions may also contain stabilizing agents and/or buffering agents and may conveniently be provided in various dosage unit ampoules.

Suitable doses for oral administration of the compounds of the invention are 1–300 mg 1 to 4 times a day, preferably 20–80 mg 1 to 4 times a day.

Methods of Preparation

The compounds of the invention may be prepared by any of the following methods;

A. A compound of formula I where A is

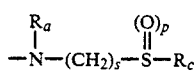

wherein X, Y, Z, n, s, p,
$R_a$ and $R_c$ are defined as above can be obtained by a reaction of a compound of the formula

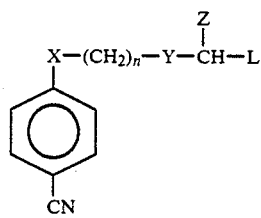

where L is a leaving group such as Cl, Br, I, mesyloxy or tosyloxy
and a compound of the formula

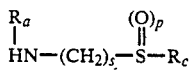

The reaction is typically carried out in a suitable organic solvent such as acetonitrile or N,N-dimethylformamide. A suitable organic or inorganic base such as triethylamine or potassium carbonate is added. The mixture is then heated to 40°–100° C. until the reaction is completed after which the product can be isolated and purified by conventional methods.

B. The compounds of the formula I wherein A is

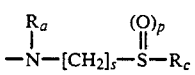

and the symbols X, Y, Z, n, s, p, $R_a$ and $R_c$ are defined as above, can be obtained by reaction of a compound of the formula

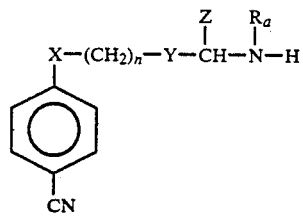

with a compound of the formula

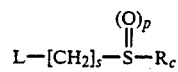

wherein L is a leaving group such as Br, Cl or I mesyloxy or tosyloxy and s, p and $R_c$ are as defined above.

The reaction is typically carried out in a suitable organic solvent such as acetonitrile, isopropanol or N,N-dimethylformamide. A suitable organic or inorganic base (acid acceptor) such as triethylamine or potassium carbonate is added to the mixture. The mixture is then heated to a temperature in the range of 40°–100° C. until the reaction is completed after which the products can be isolated and purified by conventional methods.

C. The compounds of the formula I wherein p is an integer 1 or 2 can be obtained by oxidation of a compound of the formula I wherein p is an integer 0.

When the substrate is an amine it could be neutralized with a suitable acid, e.g. p-toluene sulfonic acid in a solvent where the salt is soluble e.g. ethanol. When the sulfoxide (p=1) shall be prepared the temperature should be kept between −20°–0° C. When the sulfone (p=2) shall be prepared a temperature in the range 20°–80° C. could be used.

D. The compounds of the formula I wherein
X=O,
n=1,
Y=CHOH,
Z=H,
p=1 or 2,
$R_a$, $R_c$ and s have the meaning given above,
can be prepared by reaction of a compound of the formula

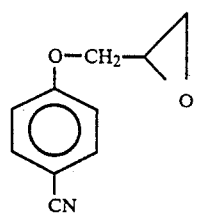

with a compound of the formula

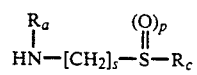

wherein $R_a$, $R_c$, s and p have the meanings given above.

Intermediates

The compounds of the formula

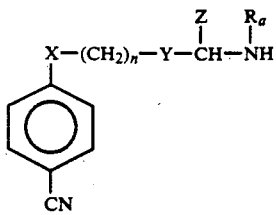

II wherein
X is O, CH$_2$, CHOH, CO, CONH, NH, S, SO or SO$_2$,
n is an integer 0, 1 or 2
Y is [CH$_2$]$_m$, CHOH, CHOCH$_3$, CHNHR or CHF,
m is an integer 0 or 1 and
R is hydrogen, methyl or ethyl,
Z is hydrogen or a saturated or unsaturated, straight or branched alkyl group containing 1–3 carbon atoms,
R$_a$ is a straight or branched hydroxy alkyl or an alkyl group containing 1–4 carbon atoms and optionally substituted by one or more fluoro atoms,
are valuable intermediates for the preparation of the compounds of the formula I via the method A. These intermediates are new and constitute a part of the invention.

The compounds of formula II are prepared by reaction of a compound of the formula

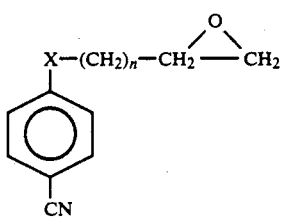

with a compound of the formula

wherein X, n and R$_a$ have the definitions given above.
Other valuable intermediates are

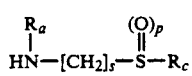

III wherein R$_a$, R$_c$, s and p have the meanings given above.
Such intermediates can generally be obtained by a reaction of a compound of the formula

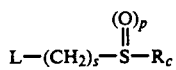

where L is Cl, Br, I, mesyloxy or tosyloxy with an amine of the formula

where P is an easily removable protective group.

A typical procedure in analogy with procedure B can be used.

WORKING EXAMPLES

EXAMPLE 1

4-[3-[ethyl[3-(phenylthio) propyl]amino]-2-hydroxypropoxy]-benzonitrile

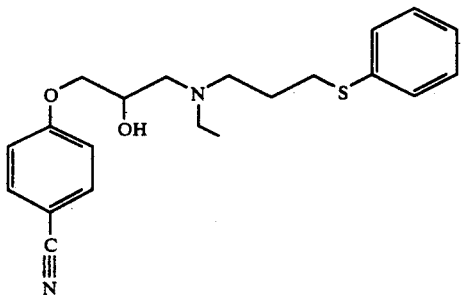

a) 4-[3-(ethylamino)-2-hydroxypropoxy]- benzonitrile 86.0 g of 4-(oxiranylmethoxy) benzonitrile was dissolved in 250 ml acetonitrile and mixed with 29.7 g ethylamine in an autoclave. The mixture was heated in a boiling water-bath over night, evaporated and the residue was dissolved in 2 M hydrochloric acid. This acid waterlayer was washed twice with ether, alkalized with 10 M sodium hydroxide and extracted with three portions of dichloromethane.

The combined organic layers were dried over sodiumsulfate and evaporated. The solid residue was recrystallized twice from a mixture of diisopropylether: acetonitrile(9:1). Yield: 57 g 4-[3-(ethylamino)-2-hydroxypropoxy]-benzonitrile.

NMR: $^{13}$C in CDCl$_3$; 14.88, 43.93, 51.28, 67.60. 70.77, 104.31, 115.26, 119.00, 133.93, 161.93 ppm b) 4-[3-[ethyl[3-(phenylthio) propyl]amino]-2-hydroxypropoxy]-benzonitrile 5.0 g of 4-[3-(ethylamino)-2-hydroxypropoxy]-benzonitrile and 4.0 g of 1-chloro-3-(phenylthio) propane was dissolved in 70 ml of acetonitrile and mixed with 6.4 g potassium carbonate and 8.0 g of sodium iodide. The mixture was refluxed over night, filtrated, evaporated and the residue was dissolved in 2 M hydrochloric acid. This acidic waterlayer was washed with two portions of diethylether, alkalized with 10 M sodium hydroxide and extracted with three portions of dichlorometane. The combined layers of dichloromethane were dried over sodium sulphate and evaporated. The oily residue was purified by column chromatography on silica gel. Yield: 2.1 g of the title compound.

NMR: $^{13}$C in CDCl$_3$; 11.04, 25.86, 31.42, 47.90, 52.32, 56.48, 65.66, 70.50, 104.22, 115.25, 119.02, 126.05, 128.88, 129.23, 133.88, 133.95, 161.90 ppm

EXAMPLE 2

4-[3-[ethyl[3-(phenylsulfinyl) propyl]amino]-2-hydropropoxy]-benzonitrile

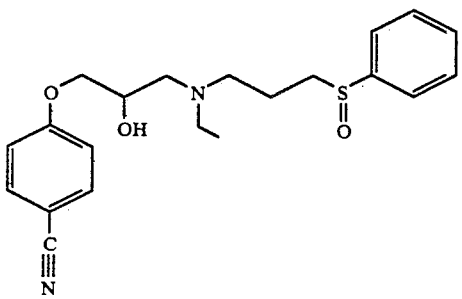

4 g of 4-[3-[ethyl[3-(phenylthio) propyl]amino]-2-hydroxypropoxy]-benzonitrile and 1 g of p-toluenesulfonic acid were mixed in 50 ml of ethanol. The mixture was cooled to −10 ° C. and 2.1 g of m-chloroperbenzoic acid was added in small portions. The mixture was stirred for 0.5 hour at −10 ° C. and one hour at room temperature and then evaporated. The residue was dissolved in dichloromethane and washed with three portions of sodium carbonate and twice with water and thereafter dried over sodium sulfate, filtrated and evaporated. The residue, 3.8 g oil was purified by column chromatography and yielded 3.1 g of the title compound.

NMR: $^{13}C$ in CDCl$_3$; 11.37, 11.49, 19.97, 20.19, 47.52, 52.14, 52.48, 54.72, 55.02, 56.25, 56.32, 66.08, 66.14, 70.55, 70.62, 115.26, 119.03, 123.84, 129.19, 130.92, 133.87, 144.03, 144.21, 162.00 ppm

EXAMPLE 3

4-[2[ethyl[3-(propylthio)propyl]amino]-1-hydroxyethyl]benzonitrile

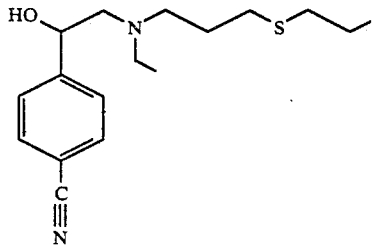

1.5 g of 4-[2-(ethylamino)-1-hydroxyethyl]-benzonitrile, 2.1 g of potassiumcarbonate, 1.7 g of 1-bromo-3-(propylthio)-propane was mixed in 50 ml acetonitrile and refluxed over night. The mixture was filtered and evaporated and the residue was dissolved in 2 M hydrochloric acid. The acidic waterlayer was washed twice with ether, alkalized with 10 M sodiumhydroxide and extracted with three portions of dichloromethane.

The combined organic layer was dried over sodiumsulphate, filtered and evaporated. The residual oil, 2.2 g, was separated by column chromatography. Yield: 1.7 g of the title compound.

NMR: $^{13}C$ in CDCl$_3$; 11.31, 13.05, 22.51, 26.68, 29.43, 33.92, 47.04, 51.81, 61.85, 68.54, 110.51, 118.39, 126.05, 131.60, 147.92 ppm.

EXAMPLE 4

4-[2-[ethyl[3-(propylsulfinyl)propyl]amino]-1-hydroxyethyl]-benzonitrile 0.9 g of 4-[2-[ethyl[3-(propylthio)propyl]amino]-1-hydroxyethyl]-benzonitrile was oxidized with 0.7 g of m-chloroperbenzoic acid in analogy with example 2. Yield: 0.7 g of the title compound.

NMR: $^{13}C$ in CDCl$_3$; 10.95, 11.07, 12.93, 15.84, 20.10, 20.22, 47.03, 49.35, 49.63, 51.64, 51.98, 54.01, 54.11, 61.49, 68.94, 110.36, 118.42, 126.17, 131.55, 148.04, 148.14 ppm.

EXAMPLE 5

2-[[3-[[3-(4-cyanophenoxy)-2-hydroxypropyl]ethylamino]propyl]thio]benzamide

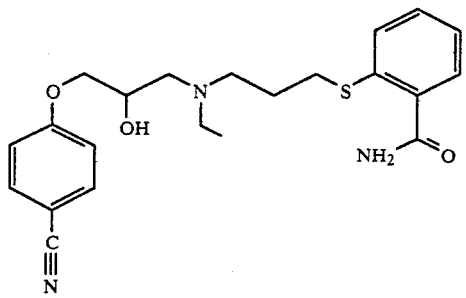

5.5 g 2-(3- chloropropylthio)benzamide, 5.3 g of 4-[3-(ethylamino) -2-hydroxypropoxy]- benzonitrile, 6.6 g potassium carbonate and 7.2 g sodiumiodide were mixed in 100 ml of acetonitrile and heated to reflux for two days. The mixture was filtered and evaporated and the residue was dissolved in 1 M sulphuric acid. The acidic water layer was then washed twice with ether, alkalized with 10 M sodiumhydroxide and extracted with dichlormethane. The organic layer was dried over sodiumsulphate, treated with active carbon, filtered and evaporated. The residue, 8.7 g, was separated by column chromatography. Yield: 4.5 g of the title compound.

NMR: $^{13}C$ in CDCl$_3$; 11.10, 26.90, 41.48, 47.37, 50.28, 58.04, 66.07, 70.38, 103.56, 114.99, 118.81, 120.09, 124.22, 125.17, 126.15, 131.45, 133.49, 139.72, 161.79, 164.98 ppm.

EXAMPLE 6

4-[3-[ethyl[3-[(4-hydroxyphenyl thio]propyl]amino]-2-hydroxypropoxy]-benzonitrile

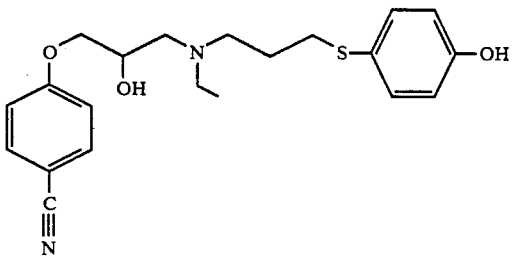

5.0g of 4-[3-(ethylamino)-2-hydroxypropoxy]-benzonitrile and 4.0 g of 4-[(3-chloropropyl)thio]-phenol was dissolved in 70 ml of acetonitrile and mixed with 6.4 g potassium carbonate and 8.0 g of sodium iodide.

The mixture was refluxed over night, filtrated, evaporated and the residue was dissolved in 2 M hydrochloric acid. This acidic waterlayer was washed with two portions of diethylether, alkalized with 10 M sodium hydroxide and extracted with three portions of dichlorometane. The combined layers of dichloromethane were dried over sodium sulphate and evaporated. The oily residue was purified by column chromatography on silica gel. Yield: 3.6 g of the title compound.

NMR: $^{13}$C in CDCl$_3$; 11.56, 26.46, 33.76, 47.60, 51.94, 55.90, 65.90, 0.52, 103.95, 115.33, 116.15, 118.97, 125.46, 133.32, 134.08, 155.71, 62.07 ppm.

EXAMPLE 7

4-[2-hydroxy-3-(4-thiomorpholinyl)propoxy]-benzonitrile

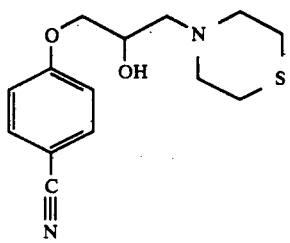

A solution of 4-(oxiranylmethoxy)benzonitrile (10 g, 56.8 mmol) and thiomorpholine (7 g, 67.8 mmol) in 2-propanol (100 ml) was stirred over night at room temperature. Solvent was evaporated. The oily residue was dissolved in hydrochloric acid (2M, 50 ml) and extracted twice with diethylether. The acid aqueous solution was treated with sodium carbonate solution. The basic-aqueous layer was extracted three times with methylene chloride. The combined organic layers were dried over magnesium sulphate and solvent was evaporated. The crude oil was crystallized from diisopropylether; methylene chloride (9:1). Yield of the title compound (8.85 g; 56%) as colourless crystals with mp. 94°–95° C.

NMR: $^{13}$C in CDCl$_3$; 27.80, 55.17, 60.81, 65.11, 70.35, 104.15, 115.18, 118,90, 133.81, 161.84 ppm.

EXAMPLE 8

4-[2-hydroxy-3-(4-thiomorpholinyl)propoxy]-benzonitrile, S-oxide

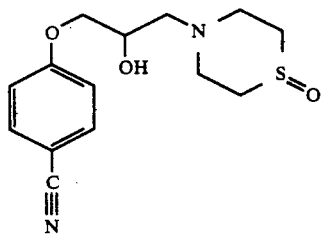

To an ice cold stirred solution of 4-[2-hydroxy-3-(4-thiomorpholinyl) propoxy]-benzonitrile (5.57 g, 20 mmol) in methylene chloride (50 ml) was added toluene-4-sulfonic acid (3.80 g, 20 mmol) and after five minutes 3-chloroperbenzoic acid (3.80 g, 22 mmol). The solution was stirred at room temperature over night. The resulting suspension was worked-up by evaporation of the solvent. The residue was treated with hydrochloric acid (2M, 20 ml) and extracted twice with diethylether. The acidic aqueous layer was treated with a sodium hydroxide solution to pH 12 and extracted with methylene chloride. The organic layer was dried over magnesium sulphate and evaporated. Yield 5.3 g of a colourless solid. Recrystallization from methylene chloride by addition of diisopropyl ether gave the title compound (4.7 g, 80%) as colourless crystals with mp. 130°–31° C.

NMR: $^{13}$C in CDCl$_3$; 43.75, 45.06, 46.15, 46.21, 60.10, 65.81, 70.19, 104.18, 115.17, 118.88, 133.83, 161.76 ppm.

EXAMPLE 9

4-[4-[(2-hydroxyethyl)[3-(propylthio)propyl]amino]-butyl]benzonitrile

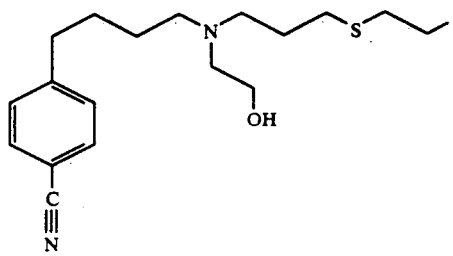

5.0 g of 4-[4-[(2-hydroxyethyl)amino]butyl]benzonitrile and 4.9 g of 1-bromo-3-(propylthio)propane were dissolved in 50 ml of isopropanol. 6.3 g of potassium-carbonate was added and the mixture was refluxed over night and thereafter filtrated and evaporated. The oily residue was purified by column chromotography. Yield: 4.3 g of the title compound.

NMR: $^{13}$C in CDCl$_3$; 13.17, 22.64, 26.45, 26.76, 28.35, 29.64, 34.04, 35.59, 52.44, 53.32, 55.52, 58.40, 109.32, 118.69, 128.67, 131.80, 147.77 ppm.

EXAMPLE 10

4-[4-[(2-hydroxyethyl(3-(propylsulfinyl)propyl)amino]-butyl]benzonitrile

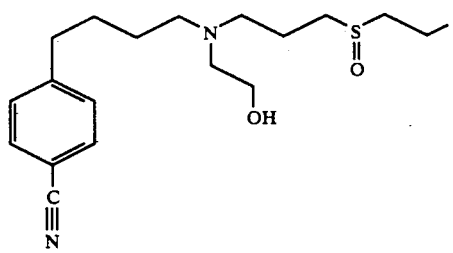

3.1 g of 4-[4- [(2-hydroxyethyl)[3-(propylthio)propyl]amino]butyl]benzonitrile was oxidized with 2.2 g of m-chloroperbenzoic acid in analogy with example 2. The yield was 0.8 g of the title compound.

NMR: $^{13}$C in CDCl$_3$; 13.27, 16.18, 20.45, 26.48, 28.52, 35.75, 50.01, 52.84, 53.48, 54.57, 55.82, 58.70, 109.54, 118.88, 129.02, 132.01, 147.84 ppm.

EXAMPLE 11

4-[[3-[ethyl[3-(propylthio)propyl]amino]-2-hydroxypropyl]amino]-benzonitrile

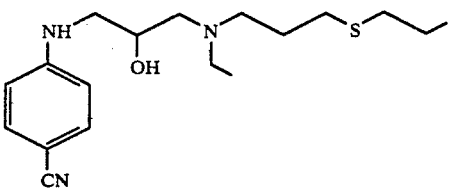

A solution of 4- [Oxiranylmethyl)amino]benzonitrile (4.7 g, 27 mmol) and N-ethyl- 3-(propylthio) -1-propanamine (4.4 g, 27 mmol) in 2-propanol (50 ml) was refluxed over night. The solvent was evaporated and the residue was purified by column chromatography on silica gel. Yield: 3.2 g of the title compound.

NMR: $^{13}$C in CDCl$_3$; 11.50, 13.25, 22.70, 26.86, 29.67, 34.15, 46.55, 47.44, 52.26, 57.33, 65.62, 98.15, 112.17, 120.30, 133.38, 151.47.

EXAMPLE 12

4-[[3-[ethyl[3-(propylsulfinyl)propyl]amino]-2-hydroxypropyl]amino]-benzonitrile

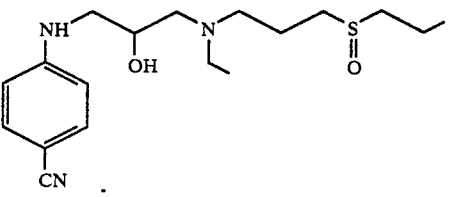

A solution of 4-[[3-[ethyl[3-(propylthio)propyl]amino]-2-hydroxy-propyl]amino]-benzonitrile (2.0 g, 5.9 mmol) and toluene-4-sulfonic acid (2.3 g, 11.9 mmol) in ethanol (50 ml) was stirred ½ h at room temperature. The mixture was cooled to −10 °C. and solid 3-chloroperbenzoic acid was added during ½ h. The solution was stirred for 1 h at room temperature. Solid calcium hydroxide (1.2 g, 16.4 mmol) was added, followed by stirring for 15 minutes. Filtration and evaporation gave an oily residue. Purification by column chromatography on silica gel yielded 1.0 g of the title compound.

NMR $^{13}$C in CDCl$_3$; 11.17, 11.34, 13.15, 16.09, 20.47, 46.58, 46.64, 47.52, 47.60, 49.79, 50.00, 52.21, 52.40, 54.40, 54.46, 57.40, 57.43, 65.96, 66.02, 97.98, 112.13, 120.33, 133.33, 151.56

EXAMPLE 13

4-Cyano-N-[N'-isopropyl-N'-(3-propylthio)propyl]aminoethylbenzamide

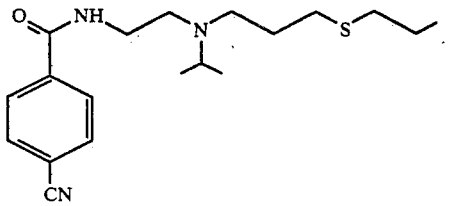

a) N-Acetyl-N'-isopropyl-N'-benzyldiaminoethane

A solution of 19.2 g (0.1 mol) of N-acetyl-N'benzyldiaminoethane and 12.3 g (0.1 mol) of 2-bromopropane in 150 ml of acetonitrile was refluxed together with 15 g of finely ground K$_2$CO$_3$ overnight. The solution was filtered and evaporated to dryness. Yield 23.5 g (0.1 mol, 100%) of a yellow oil.

NMR: $^{13}$C in CDCl$_3$; 17.89, 23.03, 37.40, 48.06, 49.87, 53.69, 126.85, 128.29, 128.48, 140.75, 169.71.

b) N-Acetyl-N'-isopropyldiaminoethane

To a solution of 23.5 g (0.1 mol) of N-acetyl-N'-isopropyl -N'-benzyldiaminoethane in 200 ml of ethanol was added 1.5 g of Pd/C (5%), and the solution was hydrogenated at atmospheric pressure (2.3 L of H$_2$ absorbed). The solution was filtered and evaporated to dryness. Yield 14.5 g (0.1 mol, 100%) of a pale yellow oil.

NMR $^{13}$C in CDCl$_3$: 21.07, 23.13, 38.09, 45.67, 49.74, 171.09.

c) N-Acetyl-N'-isopropyl-N'-(3-propylthio)propyldiaminoethane

A solution of 14.5 g (0.1 mol) of N-acetyl-N'-isopropyldiaminoethane and 19.8 g (0.1 mol) of 1-bromo-(3-propylthio)propane was refluxed overnight with 18 g (0.13 mol) of K$_2$CO$_3$ in 200 ml of acetonitrile. The solution was filtered and evaporated to dryness. Yield 15.0 g (58 mmol, 58%) of a brownish-yellow oily liquid.

NMR: $^{13}$C in CDCl$_3$; 13.44, 17.89, 22.93, 23.25, 28.60, 29.90, 34.41, 37.54, 48.00, 48.54, 49.54, 169.85.

d) N-Isopropyl-N-(propylthio)propyldiaminoethane

A solution of 15.0 g (58 mmol) of N-acetyl-N'-isopropyl-N'-(3-propylthio)propyldiaminoethane and 3.83 g (58 mmol; 85%) of KOH in 100 ml of n-butanol was refluxed for 20 h. The butanol was removed by evaporation and the remainder was dissolved in water. The water solution was extracted with 4×50 ml of ether. The etherphase was dried (Na$_2$SO$_4$) and evaporated to dryness. Yield 10.2 g (47 mmol, 81%) of a yellow oil.

NMR: $^{13}$C in CDCl$_3$; 13.35, 17.94, 23.11, 28.97, 29.72, 34.11, 40.53, 48.85, 49.96, 52.58.

e) 4-Cyano-N-[N'-isopropyl-N'-(3-propylthio)propyl]aminoethylbenzamide

To a cooled (−5° C.) slurry of 6.8 g (46.2 mmol) of 4-cyanobenzoic acid in 100 ml of ethyl acetate was added 6.32 g (46.2 mmol) of isobutyl chloroformate over a ½ h period. The resulting slurry was stirred for ½ additional hour, and then 10.1 g (46.2 mmol) of N-isopropyl-N-(propylthio)propyldiaminoethane was added at −5° C. After stirring 1 h the clear solution was poured into water, and the mixture extracted with 4×50 ml of ether. The ether solution was dried (Na$_2$SO$_4$) and evaporated. The product was purified chromatographically (Si-gel, CH$_2$Cl$_2$/MeOH 9/1). Yield 10.1 g (29.1 mmol, 63%) of a very pale yellow oily liquid.

NMR: $^{13}$C in CDCl$_3$; 13.37, 17.82, 22.82, 28.30, 29.90, 34.39, 37.67, 47.55, 48.45, 49.46, 114.74, 117.99, 127.52, 132.31, 138.65, 165.23.

EXAMPLE 14

4-[3-[ethyl[3-[(4-hydroxyphenyl)sulfinyl]propyl]amino]-2-hydroxypropoxyl]-benzonitrile

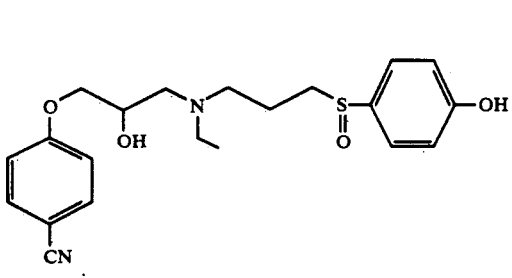

a)
4-[3-[[3-[[4-(acetyloxy)phenyl]thio]propyl]ethylamino]-2-hydroxypropoxy]benzonitrile To a solution of sodium hydroxide (0.9 g in 25 ml dioxan) was added 4-[3-[ethyl[3-[(4-hydroxyphenyl)thio]propyl]amino]-2-hydroxypropoxy]-benzonitrile (3.4 g, 8.8 mmol) and tetrabutylammonium hydrogen sulphate. To the solution was added dropwise acetylchloride (0.78 g, 10 mmol) dissolved in dioxan (10 ml). The solution was stirred at room temperature for 2 h. After filtration and evaporation the residue was dissolved in methylene chloride, treated with charcoal and filtered through Celite. The solvent was evaporated. The yield of the title compound was 3.8 g.

b)
4-[3-[ethyl[3-[(4-hydroxyphenyl)sulfinyl]propyl]amino]-2-hydroxypropoxy]-benzonitrile A solution of 4-[3-[[3-[[4-(acetyloxy)phenyl]thio]propyl]ethylamino] -2-hydroxypropoxy]-benzonitrile (3.80 g, 8.8 mmol) and toluene-4-sulfonic acid (1.67 g, 8.8 mmol) in ethanol (100 ml) was stirred and chilled to −15° C. To the chilled solution was added a solution of 3-chloroperbenzoic acid (2.05 g, 8.8 mmol) in ethanol (10 ml). The solution was stirred at room temperature for 2 h. Sodium hydroxide (8.8 g, 0.22 mol) was added and the solution was stirred for 1 h. The pH was adjusted to about 7 with hydrochloric acid. After evaporation the residue was treated with 2M hydrochloric acid and washed with diethylether. The acidic aqueous layer was treated with sodium hydroxide solution to pH =9 and extracted with three portions of ethyl acetate. The combined ethyl acetate fractions were dried over sodium sulfate and evaporated. The oily residue was purified by column chromatography on silica gel. Yield: 0.9 g of the title compound.

NMR: $^{13}C$ in $CDCl_3$; 11.29, 11.40, 20.34, 20.52, 47.53, 52.09, 52.37, 54.47, 54.72, 56.06, 66.21, 70.42, 70.46, 104.09, 115.28, 116.70, 119.08, 126.35, 131.68, 131.82, 133.94, 160.41, 161.98, 186.69.

EXAMPLE 15

4-[3-[ethyl[3-[(3-fluorophenyl)thio]propyl]amino]-2-hydroxypropoxy]-benzonitrile

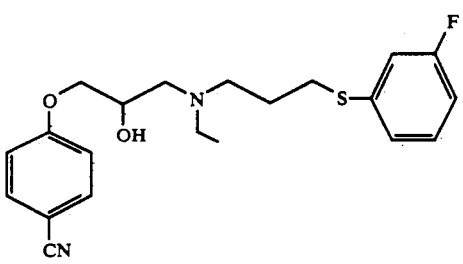

a) 1-chloro-3-[3-fluorophenyl)thio]-propane

A slurry of 1-bromo-3-chloro-propane (6.5 g, 41 mmol), 3-mercaptofluorobenzene (5.3 g, 41 mmol) and potassium carbonate (11.3 g) in acetonitrile (60 ml) was refluxed over night. The slurry was filtered and evaporated. The residue was dissolved in methylene chloride, washed with sodium hydroxide, dried over sodium sulfate and evaporated. Yield: 8.4 g of the title compound.

NMR: $^{13}C$ in $CDCl_4$; 30.29, 31.55, 43.12, 112.76, 112.84, 113.01, 115.44, 115.63, 124.36, 130.15, 130.21, 138.32, 138.90, 161.89, 162.88.

b)
4-[3-[ethyl[3[(3-fluorophenyl)thio]propyl]amino]-2-hydroxopropoxy]-benzonitrile A slurry of 4-[3-(ethylamino)-2-hydroxy]benzonitrile (5 g, 23 mmol) and 1-chloro-3-[(3-fluorophenyl) thio]-propane (4.65 g, 23 mmol) and potassium carbonate (6.35 g) in acetonitrile (70 ml) was refluxed over night. The slurry was filtered and evaporated. The residue was dissolved in 2 M hydrochloric acid, washed with diethylether and extracted with methylene chloride (3×75 ml). The extract was treated with 2 M sodium hydroxide, the phases were separated and the organic phase was dried over sodium sulfate and evaporated. Yield: 6.85 g of the title compound.

NMR: $^{13}C$ in $CDCl_3$; 11.43, 26.22, 30.77, 47.48, 52.13, 56.05, 65.94, 70.43, 103.87, 112.27, 112.44, 114.74, 114.93, 115.08, 118.88, 122.78, 129.22, 129.82, 133.64, 138.99, 161.87, 163.58

Example of pharmaceutical composition

The following examples illustrate the preparation of pharmaceutical compositions of the invention. The wording "active substance" denotes a compound according to the present invention or a salt thereof.

Formulation A. Soft gelatin capsules 500 g of active substance were mixed with 500 g of corn oil, whereupon the mixture was filled in soft gelatin capsules, each capsule containing 100 mg of the mixture (i.e. 50 mg of active substance).

Formulation B. Soft gelatin capsules 500 g of active substance were mixed with 750 g of pea nut oil, whereupon the mixture was filled in soft gelatin capsules, each capsule containing 125 mg of the mixture (i.e. 50 mg of active substance).

Formulation C. Tablets 50 kg of active substance were mixed with 20 kg of silicic acid of the trademark Aerosil. 45 kg of potato starch and 50 kg of lactose were mixed therewith and the mixture was moistened with a starch paste prepared from 5 kg of potato starch and distilled water, whereupon the mixture was granulated through a sieve. The granulate was dried and sieved, whereupon 2 kg of magnesium stearate was mixed into it. Finally the mixture was pressed into tablets each weighing 172 mg.

Formulation D. Effervescing tablets 100 g of active substance, 140 g of finely divided citric acid, 100 g of finely divided sodium hydrogen carbonate, 3.5 g of magnesium stearate and flavouring agents (q.s.) were mixed and the mixture was pressed into tablets each containing 100 mg of active substance.

Formulation E. Sustained release tablet 200 g of active substance were melted together with 50 g of stearic acid and 50 g of carnauba wax. The mixture thus obtained was cooled and ground to a particle size of at most 1 mm in diameter. The mixture thus obtained was mixed with 5 g of magnesium stearate and pressed into tablets each weighing 305 mg. Each tablet thus contains 200 mg of active substance.

Formulation F. Injection solution

| | |
|---|---|
| Active substance | 3.0 mg |
| Sodium pyrosulfite | 0.5 mg |
| Disodium edetate | 0.1 mg |
| Sodium chloride | 8.5 mg |
| Sterile water for injection | ad 1.0 ml |

Formulation G. Hard gelatine capsules 10 g of active substance was mixed with 400 g of lactose and finally 2 g of magnesium stearate was added. The mixture was then filled in hard gelatine capsules, each capsule containing 206 mg of the mixture (i.e. 5 mg of active substance).

Formulation H. Tablets 50 g of active substance was mixed with 1500 g of lactose, 200 g of microcrystalline cellulose and 10 g magnesium stearate. Tablets of 5 mg active substance with a core weight of 176 mg were finally compressed.

Pharmacology

Drugs which cause a delay of the repolarization process, thereby prolonging the period during which the heart is unable to respond to a new stimulus (the so called effective refractory period) are said to exert a Class III antiarrhythmic action (Vaughan Williams, 1970, 1984). This effect can be recorded as a prolongation of the action potential of myocardial cells, and can be measured directly in transmembrane potential recordings or indirectly in the monophasic action potential. The compounds belonging to this invention have been studied with the latter technique.

Male guinea-pigs are anaesthetized with barbiturate and ventilated with room air under blood gas control. The heart is exposed by thoracotomy and the vagal nerves are cut. A standard electrocardiogram is recorded from skin electrodes, and a monophasic action potential (MAP) is recorded from the epicardial surface of the ventricles, usually from the left one, by a specially designed bipolar electrode, which is gently pressed against the epicardial surface or attached by use of suction pressure. A local electrocardiogram from the area of the MAP electrode is also obtained (between the peripheral electrode and reference from the skin electrodes). Arterial blood pressure is recorded via an arterial cathether in one femoral artery, and intravenous lines are used for infusion of barbiturate and test substance. Since the duration of the depolarization of the heart cells (the MAP duration) is dependent on the frequency, the evaluation of a drug effect must be made at a constant frequency. For that purpose a pacing electrode is attached to the left atrium, and the heart can be electrically stimulated at a constant frequency slightly above the normal sinus node frequency.

The monophasic action potential duration at 75% repolarization is used for primary screening.

All experiments are done under $\beta$-adrenoceptor blockade, achieved by pretreatment with 0.5 mg/kg propranolol.

The test substances are administered intravenously during 30 seconds in increasing doses at exact, predetermined intervals and recordings are made at exact intervals after dosing, both on a Mingograph recorder and on tape for later analysis of the signals by a custom-designed computer program. Dose-respons curves are constructed for the different variables, and the doses needed to obtain 10 and 20 per cent prolongation of the MAP duration are derived by interpolation. The dose giving 20 per cent increase of the MAP duration ($D_{20}$ MAP) is used as a measure of potency.

Selected compounds are subject to further testing in anaesthetized and chronically instrumented conscious dogs, in which effects on atrial and ventricular refractoriness are also recorded.

TABLE 1

| Substance according to Example No | $D_{20}$ MAP | VERP |
|---|---|---|
| Ex. 2 | 7.2 | n.t. |
| Ex. 9 | 7.2 | n.t. |

$D_{20}$-MAP = $-$log dose (moles/kg) giving 20 per cent increase of the MAP duration in anaesthetized guinea-pigs (see screening method).

Change in ventricular refractoriness (VERP) in anaesthetized and conscious dogs at dose levels equivalent to $D_{20}$-MAP in guinea-pigs.

+ = prolonged VERP
n.t. = not tested

We claim:

1. A compound formula:

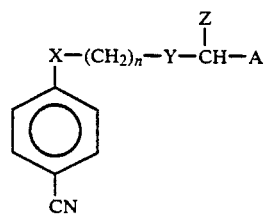

and when appropriate in the form of a racemic mixture or in the form of a stereoisomeric compound or the pharmaceutically acceptable salts thereof, in which formula, X is O, CH₂, CHOH, CO, NH, CONH wherein C is bound to the aromatic ring, n is an integer 0, 1 or 2

Y is [CH₂]ₘ, CHOH, C(OH)CH₃, CHNHR or CHF, m is an integer 0 or 1 and

R is hydrogen, methyl or ethyl,

Z is hydrogen or a straight or branched alkyl group containing 1–3 carbon atoms, an alkene or alkyne group containing 2–3 carbon atoms and one or two unsaturated bonds, A is a group:

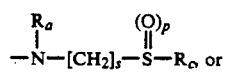

a quaternary compound thereof quarternarized with a lower alkyl group, wherein $R_a$ is a straight or branched hydroxyalkyl group containing 1 hydroxy group and 1–5 carbon atoms, or a straight or branched alkyl group containing 1–5 carbon atoms, $R_c$ is selected from the group consisting of a straight or branched alkyl group containing 1–4 carbon atoms, an alkene or alkyne group containing 2–4 carbon atoms and an unsubstituted phenyl group or a phenyl group substituted by 1–3 substituents selected from the group consisting of fluoro, hydroxy, methoxy, ethoxy, CN, CONH₂, NHSO₂CH₃, p is an integer 0, 1 or 2, r is an integer 0, 1, 2 or 3, s is an integer 2, 3, 4 or 5, with the proviso that when X is O then $R_c$ is an unsubstituted phenyl group or a phenyl group substituted by 1–3 substituents selected from the group consisting of fluoro, hydroxy, methoxy, ethoxy, CN, CONH₂, NHSO₂CH₃.

2. A compound according to claim 1 wherein

X is O, CH₂, CHOH, CONH, NH n is 0, 1

Y is CHOH, (CH₂)ₘ wherein m 0, 1

Z is hydrogen

A is a group

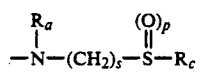

wherein $R_a$ is CH₃, C₂H₅C₃H₇, CH₂CH₂OH, s is 3, 4 p is 0, 1

$R_c$ is C₂H₅, C₃H₇, CH₂CHFCH₃, or an unsubstituted phenyl or a phenyl group substituted with OH, F, OCH₃, OC₂H₅, 3. A compound according to claim 2 wherein X is O n is 1

Y is CHOH, (CH₂)ₘ wherein m=1

Z is hydrogen

A is a group

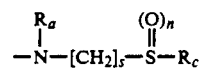

wherein $R_a$ is CH₃, C₂H₅, C₃H₇, CH₂CH₂OH s is 3 p is 0, 1

$R_c$ is an unsubstituted phenyl group or a phenyl group substituted with OH, F, OCH₃, OC₂H₅.

4. A compound according to claim 2 wherein

X is CH₂ n is 0, 1

Y is CHOH, (CH₂)ₘ where m=0, 1

Z is hydrogen

A is a group

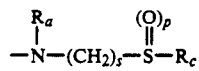

wherein $R_a$ is CH₃, C₂H₅, C₃H₇, CH₂CH₂OH s is 3 p is 0,1

$R_c$ is C₂H₅, C₃H₇, CH₂CHFCH₃

5. A compound according to claim 1 wherein

4-[3-[ethyl[3-(phenylthio) propyl]amino]-2-hydroxypropoxy]benzonitrile

4-[3-[ethyl[3-(phenylsufinyl) propyl]amino]-2-hydroxypropoxy]-benzonitrile

4-[2[ethyl[3-(propylthio)propyl]amino]-1-hydroxyethyl]benzonitrile

4-[2-[ethyl[3-(propylsulfinyl)propyl]amino]-1-hydroxyethyl]benzonitrile

2-[[3-[[3-(4-cyanophenoxy)-2-hydroxypropyl]ethylamino]-propyl]thio]benzamide

4-[3-[ethyl[3-[(4-hydroxyphenyl)thio]propyl]amino]-2-hydroxypropoxy]-benzonitrile 4-[4-[(2-hydroxyethyl)[3-(propylthio)propyl]amino]-butyl]-benzonitrile 4-[4-[(2-hydroxyethyl)[3-(propylsulfinyl)propyl]amino]butyl]benzonitrile 4-[[3-[ethyl[3-(propylthio) propyl]amino]-2-hydroxypropyl]amino]-benzonitrile 4-[[3-[ethyl[3-propylsulfinyl) propyl]amino]-2-hydroxypropyl]amino]-benzonitrile 4-cyano-N-[N'-isopropyl-N'-(3-propylthio)propyl]aminoethylbenzamide 4-[3-[ethyl[3-[(4-hydroxyphenyl)sulfinyl]propyl]amino]-2-hydroxypropoxy]-benzonitrile 4-[3-[ethyl[3-[(3-fluorophenyl)thio]propyl]amino]-2-hydroxypropoxy]-benzonitrile.

6. a pharmaceutical preparation comprising as active ingredient a a therapeutically effective amount of a compound according to any of claims 2–5 and 1 or a pharmaceutically acceptable salt or a stereoisomer thereof in a pharmaceutically acceptable carrier.

7. A pharmaceutical preparation according to claim 6 in dosage unit form.

8. A method for the treatment of cardiac arrhythmia in mammals, characterized by the administration to a host in need of such treatment of an effective amount of a compound according to any of claims 2–5 and 1 or pharmaceutically acceptable salt thereof.

* * * * *